(12) United States Patent
Lu

(10) Patent No.: US 9,452,112 B2
(45) Date of Patent: Sep. 27, 2016

(54) DENTAL COMPOSITIONS

(75) Inventor: Hui Lu, Magnolia, DE (US)

(73) Assignee: DENTSPLY International Inc., York, PA (US)

( * ) Notice: Subject to any disclaimer, the term of this patent is extended or adjusted under 35 U.S.C. 154(b) by 0 days.

(21) Appl. No.: 13/098,562

(22) Filed: May 2, 2011

(65) Prior Publication Data

US 2011/0275035 A1     Nov. 10, 2011

Related U.S. Application Data

(60) Provisional application No. 61/343,743, filed on May 3, 2010.

(51) Int. Cl.
    *A61K 6/083*     (2006.01)

(52) U.S. Cl.
    CPC ..................... *A61K 6/083* (2013.01)

(58) Field of Classification Search
    CPC .... A61K 6/083; A61K 6/0052; C08L 43/02; C08L 33/04
    USPC ................ 528/116, 118; 433/228.1; 106/35; 523/116, 118
    See application file for complete search history.

(56) References Cited

U.S. PATENT DOCUMENTS

| | | | |
|---|---|---|---|
| 5,973,022 A * | 10/1999 | Lu et al. ....................... | 523/116 |
| 5,981,620 A * | 11/1999 | Hammesfahr et al. ....... | 523/116 |
| 6,391,940 B1 * | 5/2002 | Blackwell et al. ........... | 523/115 |
| 6,660,785 B2 | 12/2003 | Klee et al. | |
| 6,693,143 B2 * | 2/2004 | Pflug ............................. | 523/116 |
| 2005/0175966 A1 | 8/2005 | Falsafi et al. | |
| 2006/0004122 A1 | 1/2006 | Hecht et al. | |
| 2007/0197683 A1 | 8/2007 | Jia et al. | |
| 2007/0299157 A1 * | 12/2007 | Sang et al. ..................... | 523/118 |
| 2008/0004365 A1 * | 1/2008 | Blackwell ........................ | 522/34 |
| 2009/0048364 A1 | 2/2009 | Liu | |
| 2009/0076189 A1 | 3/2009 | Matsushige et al. | |
| 2010/0010115 A1 | 1/2010 | Kohro et al. | |
| 2010/0041786 A1 | 2/2010 | Qian | |

FOREIGN PATENT DOCUMENTS

| | | |
|---|---|---|
| EP | 2011468 A1 | 7/2009 |
| EP | 2153811 A2 | 2/2010 |
| WO | 9811862 A1 | 3/1998 |

\* cited by examiner

*Primary Examiner* — Tae H Yoon
(74) *Attorney, Agent, or Firm* — Leana Levin; Douglas J. Hura; David A. Zdurne

(57) ABSTRACT

A self-etching and self-adhesive dental restorative composition is described herein. The composition includes a polymerizable compound having at least one phosphorus containing acidic group, a polymerizable compound having at least one carboxylic acid group, and a copolymerizable multi-functional (meth)acrylate monomers. Compositions described herein demonstrate adhesion to dentin and enamel and are useful as a cavity filler, dental pit and fissure sealants, and restoratives.

11 Claims, No Drawings

DENTAL COMPOSITIONS

This application claims priority to Provisional Application No. 61/343,743, filed May 3, 2010.

BACKGROUND

Disclosed herein are compositions related to light-curable resin based dental restorative materials that can provide self-etching and self-adhesive properties to a hard tooth structure. Conventional approaches to directly fill a dental cavity using esthetic, non-amalgam type material involve the utilization of glass-ionomer restoratives, resin-modified glass ionomers, compomers, or resin composite materials under different circumstances. The drawbacks of glass ionomers and resin-modified glass ionomers include high opacity (thus inferior esthetics), insufficient wear resistance, and insufficient fracture toughness, as compared to resin composites. The resin composite materials have improved mechanical properties, esthetic properties, and wear resistance, as compared to resin-modified glass ionomers and compomer materials. On the other hand, glass ionomer type materials can provide certain adhesive properties to a tooth structure, whereas resin-based composites require the use of a bonding agent prior to the placement of a dental composite.

The utilization of a bonding agent prior to the placement of composite requires quite a number of procedures and can be highly technique-sensitive. After removing carious tooth structure and cleaning the cavity, the conventional total-etch adhesive procedures involve applying etching gel (normally 34%~37% phosphoric etching gel) to acid-etching the tooth structure, rinsing with copious amount of water, air-drying, and if $4^{th}$ generation adhesive is used, need to apply another layer of primer followed by solvent evaporation, before the bonding agent is applied. Certain dental bonding agents require the application of multiple layers of adhesive before solvent evaporation and light curing. The procedures for $5^{th}$ generation bonding agents, such as Prime&Bond NT® and XP Bond® (available from DENTSPLY Caulk, Milford, Del.) are slightly simpler than $4^{th}$ generation as the adhesive and primer are combined into one bottle and no separate priming step is required. Self-etch type adhesive can provide simpler procedures as there is no need for etching gel application and rinsing. Nevertheless, the overall utilization of bonding agents involves multi-step procedures and adequate isolation is needed to prevent contamination by saliva and/or blood during these steps.

Although traditional methods of etching the tooth structure by using a etchant, such as about 34% to about 37% phosphoric etching gel, are quite effective for removing the smear layer and improving the substrate's roughness for bonding, under certain circumstances such a procedure can also result in disrupted dentin surface through excessive etching on the sound dentin (over-demineralization) followed by collapsed dentinal collagen fibrils. Furthermore, depending upon the dental bonding agent being used, it might not penetrate to a depth of over-demineralized dentin, which can introduce post-operation sensitivity.

U.S. Pat. No. 6,660,785 describes the synthesis of self-adhesive polymerizable monomers and their application as a water containing and a water free self-adhesive dental/medical composite were described. The dental/medical composite comprises a self-adhesive polymerizable monomer, a polymerizable monomer, an acid reactive and/or reactive and/or non-reactive filler, a diluent, a polymerization initiator and a stabilizer. As polymerization initiators are used the commonly known thermal initiators, redox initiators and/or photo initiators. The new adhesive dental composite develops adhesion to dentine of about 4 MPa. Fillers of high X-ray absorbance provide radio-opacity values greater than that of the same thickness of aluminum.

US Patent Publication No. 2006/0004122 discloses a composition which is self-adhesive to the hard tooth tissue, comprising: (A) 5 to 75 percent by weight of one or more mono or higher functional ethylenically unsaturated compounds which additionally have an acid functional group, wherein one of said compounds has a P—OH group, for instance a phosphoric, phosphonic or phosphinic acid group; (B) 2 to 50 percent by weight of one or more mono or higher functional ethylenically unsaturated compounds without any acid functional group; (C) 22.8 to 85 percent by weight of filling material(s), comprising at least one filling material that may react with component (A) in the sense of causing a ion exchange, neutralization, salt formation and/or chelate formation reaction; (D) 0.1 to 8 percent by weight of one or more initiators and optionally activators; (E) 0.1 to 20 percent by weight of further additives, for example, modifiers, wherein the weight ration in % of component (A) relative to component (B) ranges from 21 to 90:10 to 79.

US Patent Publication No. 2007/0197683 discloses a self-etching and self-adhesive dental composition, comprising a polymerizable (meth)acrylate carboxylic acid/anhydride; a copolymerizable multi-functional (meth)acrylate resin; a copolymerizable diluent monomer; and a curing system. The composition has the advantage of not requiring a separate etching and bonding step.

US Patent Publication No. 2010/0041786 discloses a dental restorative composition comprising (A) polymerizable monomer(s) having at least one phosphorus-containing acidic moiety and at least one ethylenically unsaturated group; (B) polymerizable monomer(s) having a molecular weight of 100-250, at least one hydroxyl group, and at least one ethylenically unsaturated group; (C) polymerizable monomer(s) having a molecular weight of 270-900, at least two ethylenically unsaturated groups and no acidic functional group; (D) photo-initiator(s); and (E) filler(s) each having a mean particle size of more than 0.005 microns and less than 70 microns. The weight ratio of (A+B):(C) ranges from 30:70 to 90:10, the concentration of (A) is 10-50 wt. %, the concentration of (B) is 15-60 wt. %, and the composition has a shear bond strength of at least 10 MPa to both dentin and enamel. Also provided is a method for filling a dental cavity with the composition without first treating the dental cavity with an etchant, a primer and/or an adhesive.

It is therefore quite desirable to have a single-component tooth filling material, such as polymerizable dental restorative composite, to bond to the tooth structure surrounding the cavity after treating the tooth surface with primer. It is further desirable to have a single-part, shelf-stable composition that can provide self-etching and self-adhesion to untreated tooth substrate. A self-adhesive composite that can provide adequate self-etching, self-priming, and self-adhesion to tooth, while not compromising other key properties obtainable from conventional composites is hence quite advantageous. Such dental restorative compositions can provide tremendous reduction in both placement time and technique-sensitivity, when compared with the use of bonding agent that may involve separate etching, rinsing, drying, priming, before the final adhesive placement and curing step.

SUMMARY

A self-etching and self-adhesive dental restorative composition and method of restoring a tooth cavity. The composition includes a polymerizable compound having at least one phosphorus containing acidic group and at least one polymerizable group, and a polymerizable compound having at least one carboxylic acid group and at least one polymerizable group, a copolymerizable multi-functional (meth)acrylate monomers, a glass filler system and photoinitiation system (photoinitiator and co-initiator). Compositions of the invention have good adhesion to dentin and enamel and are useful as dental pit and fissure sealants and restoratives.

DETAILED DESCRIPTION

Described herein are compositions designed to provide both self-etching and self-adhesion to dental hard tissues such as dentin and enamel. The restorative procedures can be greatly simplified as no separate etching, priming, and bonding steps are required prior to filling a tooth cavity with the disclosed restorative material. The composition in the described invention also has good mechanical properties and it can be cured by both a traditional quartz-tungsten-halogen (QTH) dental lamp and a light emitting diode (LED) dental lamp.

Disclosed are a self-etching and self-adhesive dental composition and a method of restoring a tooth cavity, sealing a pit or fissure, and repairing a restorative utilizing such a composition. The composition includes a first polymerizable compound having at least one phosphorus containing acidic group, a second polymerizable compound having at least one carboxylic acid group, and a copolymerizable multi-functional (meth)acrylate monomer, a filler system and a polymerization initiator system. Compositions disclosed herein have good adhesion to dentin and enamel, and are useful as dental pit and fissure sealants and restoratives.

In embodiments, the polymerizable compounds in the self-etching, self-adhesive composition are capable of being cured to form a crosslinked polymeric network. Such polymerizable compounds, either monomers or oligomers, have at least one free-radically active functional group. Most commonly, they contain ethylenically unsaturated functional group that is capable to participate in free radical polymerization and form cross-linked polymeric network. Specifically, the composition described herein comprises a first polymerizable compound having at least one phosphorus containing acidic group, a second polymerizable group having at least one carboxylic acid group, and a copolymerization multi-functional methacrylate monomer.

The first polymerizable compound with at least one phosphorus containing acidic group may have an ethylenically unsaturated functional group and phosphorus containing acidic group, such as phosphoric, phosphonic, or phosphinic acid. Examples of suitable free radically polymerizable compounds having at least one phosphorus containing acidic group include, but are not limited to, 2-(methacryloyloxyethyl)phenyl hydrogenphosphate (Phenyl-P), 2-hydroxyethyl methacryl dihydrogenphosphate (HEMA Phosphate), glycerol phosphate dimethacrylate (GPDM), dipentaerythritiol pentacrylate phosphoric acid ester (PENTA), di-2-hydroxyethyl methacryl hydrogenphophate (di-HEMA Phosphate). The first polymerizable compound having at least one phosphorus containing acidic group may be present in the composition in an amount of from about 3 weight percent to about 50 weight percent of the resin matrix composition (not including filler particles), such as from about 5 weight percent to about 45 weight percent or from about 10 weight percent to about 40 weight percent of the resin matrix.

The second polymerizable compound having at least one carboxylic acid group may be a free radically polymerizable compound such as 2,5-dimethacryloyloxyethyloxycarbonyl-1,4-benzenedicarboxylic acid (PMDM), 4,4'-Oxydiphenylether 1,1',6,6'-tetracarboxylic acid-1,1'-(2-methacryloxy)dimethacrylate (OEMA), butan-1,2,3,4-tetracarboxylic acid di-2-hydroxyethylmethacrylate ester (TCB), 2,5-bis(1,3-dimethacryloyloxyprop-2-loxycarbonyl)benzene-1,4-dicarboxylic acid (PMGDM), methacroloxyethyl phthalate, N-methacryloyl-5-aminosalicylic acid (5-NMSA), 4,4'-dimethacryloyloxyethyloxycarbonylbiphenyl-3,3'-dicarboxylic acid (BPDM); N-phenylglycine glycidyl methacrylate, 4-acryloylethyl trimellitic acid, 4-methacryloyloxyethyl trimellitic acid (4-MET). The second polymerizable compound having at least one carboxylic acid group may be present in the resin matrix in an amount of from about 1 weight percent to about 50 weight percent of the composition, such as from about 2 weight percent to about 40 weight percent or from about 5 weight percent to about 35 weight percent of the resin matrix.

The copolymerizable multi-functional (meth)acrylate monomer may be a free radically polymerizable compound, such as mono-, di- or multi-methacrylates and acrylates such as methyl methacrylate, isopropyl methacrylate, ethyl acrylate, triethyleneglycol dimethacrylate, n-hexyl acrylate, stearyl acrylate, allyl acrylate, glycerol diacrylate, glycerol triacrylate, ethyleneglycol diacrylate, diethyleneglycol diacrylate, tetraethylene glycol di(meth)acrylate, 1,3-propanediol diacrylate, 3-(acryloyloxy)-2-hydroxypropyl methacrylate, 1,3-propanediol dimethacrylate, trimethylolpropanetri (meth)acrylate, 1,2,4-butanetriol trimethacrylate, 1,4-cyclohexanediol diacrylate, 1,6-hexanediol di(meth) acrylate, pentaerythritol triacrylate, pentaerythritol tetraacrylate, pentaerythritol tetramethacrylate, sorbitol hexacrylate, 2,2-bis[4-(2-hydroxy-3-acry loyloxypropoxy) phenyl]propane; 2,2-bis[4-(2-hydroxy-3-methacryloy loxypropoxy)phenyl]propane (Bis-GMA); 2,2-bis[4-(acryloyloxy-ethoxy)phenyl]propane; 2,2-bis[4-(methacryloyloxy-ethoxy)phendyl]propane (or ethoxylated bisphenol A-dimethacrylate) (EBPADMA), polycarbonate dimethacrylate (PCDMA), 2,7,7,9,15-pentamethyl-4, 13 dioxo-3, 14 dioxa-5,12-diaza hexadecane-1, diyldimethacrylate, urethane di(meth)acrylate (UDMA), bis-acrylates and bis-methacrylates of polymethylene glycols. The copolymerizable multi-functional (meth)acrylate monomer may be present in the composition in an amount of from about 50 weight percent to about 95 weight percent of the resin matrix, such as from about 60 weight percent to about 90 weight percent or from about 65 weight percent to about 90 weight percent of the resin matrix.

The self-etching and self-adhesive composition disclosed herein further comprises one or more types of filler particles that are suitable for use in dental compositions. Filler particles are critical components to the composition described herein. Fillers that are suitable for use in the composition described herein provide the composite with desired physical and curing properties, such as increased strength, modulus, hardness, reduced thermal expansion and polymerization shrinkage, and also provide a stable shelf life such that no adverse reaction occurs between the filler particles with any of the resin matrix's organic compounds in composition during storage or transportation, and before the intended shelf-life is reached.

Examples of suitable filler particles include, but are not limited to, strontium silicate, strontium borosilicate, barium silicate, barium borosilicate, barium fluoroalumino borosilicate glass, barium alumino borosilicate, calcium silicate, calcium alumino sodium fluoro phosphor-silicate lanthanum silicate, alumino silicate, and the combination comprising at least one of the foregoing fillers. The filler particles can further comprise silicon nitrides, titanium dioxide, fumed silica, colloidal silica, quartz, kaolin ceramics, calcium hydroxy apatite, zirconia, and mixtures thereof. Examples of fumed silica include OX-50 from DeGussa AG (having an average particle size of 40 nm), Aerosil R-972 from DeGussa AG (having an average particle size of 16 nm), Aerosil 9200 from DeGussa AG (having an average particle size of 20 nm), other Aerosil fumed silica might include Aerosil 90, Aerosil 150, Aerosil 200, Aerosil 300, Aerosil 380, Aerosil R711, Aerosil R7200, and Aerosil R8200, and Cab-O-Sil M5, Cab-O-Sil TS-720, Cab-O-Sil TS-610 from Cabot Corp.

The filler particles used in the composition disclosed herein may be surface treated before they are blended with organic compounds. The surface treatment using silane coupling agents or other compounds are beneficial as they enable the filler particles to be more uniformly dispersed in the organic resin matrix, and also improve physical and mechanical properties. Suitable silane coupling agents include 3-methacryloxypropyltrimethoxysilane, methacryloxyoctyltrimethoxysilane, styrylethyltrimethoxsilane, 3-mercaptopropyltrimethoxysilen, and mixtures thereof.

Fillers may be present in amounts of from about 40 weight percent to about 85 weight percent of the self-etching and self-adhesive composition, such as from about 45 weight percent to about 80 weight percent or from about 50 weight percent to about 75 weight percent of the self-etching and self-adhesive composition.

The filler particles can have a particle size of from about 0.002 microns to about 25 microns. In one embodiment, the filler can comprise a mixture of a micron-sized radiopaque filler such as barium alumino fluoro borosilicate glass (BAFG, having an average particle size of about 1 micron) with nanofiller particles, such as fumed silica such as OX-50 from DeGussa AG (having an average particle size of about 40 nm). The concentration of micron-size glass particles can range from about 50 weight percent to about 75 weight percent of the self-etching and self-adhesive composition, and the nano-size filler particles can range from about 1 weight percent to about 20 weight percent of the self-etching and self-adhesive composition.

The self-etching and self-adhesive composition described herein further contains a polymerization initiator system. The initiator is not particularly limited and may be a photoinitiator. The present composition may employ a dual-photoinitiator system having camphorquinone (CQ) and diphenyl (2,4,6-trimethylbenzoyl)phosphine oxide (L-TPO), which proves to be an effective combination in an effective concentration to be compatible with an amine polymerization accelerator, as described below.

The polymerization photoinitiators (the combination of CQ and L-TPO) are present in an amount of from about 0.05 weight percent to about 1.00 weight percent, such as from about 0.08 weight percent to about 0.50 weight percent or from about 0.10 weight percent to about 0.25 weight percent of the self-etching and self-adhesive composition. Using such a small amount of a polymerization photoinitiators decreases the potential discoloration of the composition. By contrast, compositions containing a high concentration a photoinitiator are more likely to be discolored.

Other diketone type photoinitiator such as 1-phenyl-1,2 propanedione (PPD), and phosphine oxide type photoinitiator such as Ciba-Geigy's bis(2,4,6-trimethylbenzoyl)-phenylphosphohine oxide (Irgacure 819), BASF's ethyl 2,4,6-trimethylbenzylphenyl phosphinate (Lucirin LR8893X), may also be used.

The polymerization initiator system of the self-etching and self-adhesive composition described herein may further include a polymerization accelerator, which may be a tertiary amine. One example of a suitable tertiary amine is ethyl 4-(dimethylamino)benzoate (EDAB). Other tertiary amines that may be used include 2-(ethylhexyl)-4-(N,N-dimethylamino)benzoate, dimethyl aminobenzoic acid ester, triethanol amine, N,N,3,5,N,3,5-tetramethyl aniline, 4-(dimethyl amino)-phenethyl alcohol, dimethyl aminobenzoic acid ester, 4-(N,N-dimethylamino)benzoic acid, sodium benzenesulfinate, and the like.

However, due to the presence of an acidic adhesion promoting monomer/oligomer such as dipentaerythritiol pentacrylate phosphoric acid ester (PENTA), the compatibility between the amine polymerization accelerator and the adhesion-promoting monomer/oligomer needs to be carefully considered. The self-etching and self-adhesive composition described herein may employ a polymerization accelerator, such as dimethylaminobenzonitrile, which has showed fairly good compatibility with the acidic monomers.

The polymerization accelerator may be present in an amount of from about 0.03 weight percent to about 0.18 weight percent of the self-etching and self-adhesive composition, such as from about 0.04 weight percent to about 0.15 weight percent or from about 0.05 weight percent to about 0.12 weight percent of the self-etching and self-adhesive composition. The compositions disclosed herein are capable of being activated by a curing light having a wavelength of from about 380 nm to about 500 nm.

The self-etching and self-adhesive composition described herein may further include additives in order to provide specifically desired features. These additives include ultraviolet stabilizers, fluorescent agents, opalescent agents, pigments, viscosity modifiers, fluoride-releasing agents, antimicrobial agents, polymerization inhibitors, and the like. Examples of antimicrobial agents include zinc oxide, triclosan, chlorhexidine, 12-methacryloyloxydodecyl-pyridinium bromide (MDPB), silver, copper, titanium oxide, and quaternary ammonium polymethylenimine nanoparticles. Typical polymerization inhibitors for a free radical system may include hydroquinine monomethyl ether (MEHQ), butylated hydroxytoluene (BHT), tertiary butyl hydro quinine (TBHQ), hydroquinone, phenol, butyl hydroxyanaline, and the like. The inhibitors act as free radical scavengers to trap free radicals in the composition and to extend the shelf life stability of the composition. The polymerization inhibitors, if present, may be present in amounts of from about 0.001 weight percent to about 1.5 weight percent of the self-etching and self-adhesive composition, such as from about 0.005 weight percent to about 1.1 weight percent or from about 0.01 weight percent to about 0.08 weight percent of the self-etching and self-adhesive composition. The composition may include one or more polymerization inhibitors.

The self-etching and self-adhesive composition disclosed herein may be made by any known and conventional method. In embodiments, the composition is made by mixing the components together at a temperature of from about 20° C. to about 60° C., such as from about 23° C. to about 50° C. The monomers, photoinitiators, accelerators, and other additives can be blended first to form a paste of a uniform mixed resin blend. The paste can be prepared by mixing the components for a total of about 30 seconds to about 5 minutes, such as from about 1 minute to about 3 minutes or about 1.5 minutes, on a speedmixer, such as a Flack-Tec at room temperature (from about 23° C. to about 27° C.), followed by further mixing in a Ross Mini Mixer that is equipped with temperature and vacuum control, for a time of from about 20 minutes to an hour, such as from about 30 minutes to 50 minutes or about 40 minutes, under from about 20 to about 27 inches Hg vacuum at room temperature (from about 23° C. to about 27° C.) or further mixing in the Ross Mini Mixer takes place for a time of from about 10 minutes to about 30 minutes, such as from about 15 minutes to about 25 minutes or about 20 minutes, under from about 20 to about 27 inches Hg vacuum at an elevated temperature of from about 40° C. to about 60° C., such as from about 45° C. to about 55° C. or about 50° C. In alternative embodiments, the paste may be mixed in a Ross Mini Mixer for a time of from about 40 minutes to an hour, under from about 20 to about 27 inches Hg vacuum at an elevated temperature of from about 40° C. to about 60° C., such as from about 45° C. to about 55° C. or about 50° C., without initially using a speedmixer, as described. In yet further embodiments, the paste may be mixed on Resodyn Acoustic Mixer for a time of from about 30 minutes to about 60 minutes, such as from about 35 minutes to about 55 minutes or about 45 minutes under from about 20 to about 27 inches Hg vacuum at a temperature of from about 18° C. to about 30° C., such as 20° C. to about 27° C. or 23° C.

The self-etching and self-adhesive composition disclosed herein is suitable for use in filling a tooth cavity. After the dental practitioner removes the carious portion of the tooth structure and cleans the created tooth cavity, the composition disclosed herein is applied directly to the tooth structure. To achieve effective self-etching on tooth substrate, the substrate needs to be moist after cleaning. In one method, the self-adhesive composition is applied onto the tooth structure surface and left on the surface undisturbed for certain period of conditioning time, from 10 to 20 seconds to facilitate self-etching. Alternately, the described self-etching, self-adhesive composition can also be gently agitated after being applied on the surface with micro brush or applicator, for certain period of time, from 10 to 20 seconds to facilitate self-etching. Unlike conventional dental compositions that are known in the art, a separate bonding agent and separate etching gel are not necessary and are not placed on the tooth structure prior to application of the disclosed composition. Instead, as described herein the disclosed self-etching and self-adhesive composition is applied directly to the prepared tooth structure.

The composition described herein is not only suitable for use as cavity-filling material to fill a cavity without first applying an acidic etchant, a primer, or an adhesive to the tooth substrate. The self-etching and self-adhesive composition described herein can also be used as a self-etching, self-adhesive base/liner for lining a cavity without first applying an acidic etchant, a primer, or an adhesive to the tooth substrate to the tooth substrate. In yet further embodiments, the self-etching and self-adhesive composition described herein may be used as pit and fissure sealant, or as a repair material for damaged restorations.

One unique and innovative feature of the self-etching and self-adhesive compositions described herein is that it does not require a separate adhesive placement/curing steps before its placement (therefore no separate etchant, primer, or adhesive is needed). The self-etching and self-adhesive compositions also adapt to the cavity wall quite well without the use of hand instruments and is very user friendly as it provides considerable reduction in both placement time and technique-sensitivity, when compared with the use of a separate adhesive placement/curing steps that may involve etching, rinsing, drying, priming, before the final bonding agent can be applied and cured.

Test Methods

Notched-Edge Shear Bond Strength: Freshly extracted, caries-free and un-restored human molars were used. Teeth were sectioned longitudinally through the mesial, occlusal, and distal surfaces using a water-cooled diamond grit cutting disc. The sectioned molars were then mounted in a cylindrical block using cold-cure acrylics, with the buccal surface exposed. The exposed surface was then coarse ground on a model trimmer until a flat dentin or enamel surface was exposed. Prior to the bonding of specimen, tooth was wet-ground on grinding wheel under running water use 120-grit SiC sanding paper, followed by 320-grit SiC sanding paper, until the surface is even and smooth when visually inspected. The Notched-Edge bonding jig contains a cylindrical plastic mold resulting in samples with a defined bonding area (diameter 2.38 mm). The herein described self-etching and self-adhesive restorative composite is then carefully placed into the center of the mold, without any bonding agent or primer being applied to the substrate first. After light curing 550 mW/cm$^2$ for 20 seconds, the specimen was then carefully removed from mold. Specimens were stored in 37° C. DI-water for 24 hour before SBS testing. SBS test was performed on Instron Universal Tester 4400R at a crosshead speed of 1 mm/min. A minimum of seven specimens were tested for each set of sample.

Flexural Strength: Specimens for 3-point bending flexural test were prepared according to ISO 4049. Sample were filled into 25 mm×2 mm×2 mm stainless steel mold, then covered with Mylar film and cured using Spectrum 800 (DENTSPLY Caulk) halogen lamp at intensity of 550 mW/cm$^2$ for 4×20 seconds uniformly across the entire length of the specimen. The set specimens were stored in deionized water at 37° C. for 24 hours prior to the test. Flexural test was conducted using an Instron Universal Tester Model 4400R with crosshead speed 0.75 mm/min under compressive loading mode. A minimum of six specimens were tested for each set of sample.

Compressive Strength: Samples were filled into Ø4×7 mm Teflon molds and sandwiched between two Mylar cover films, then cured using Spectrum 800 lamp at intensity of 550 mW/cm$^2$ on both ends. The set specimens were stored in deionized water at 37° C. for 24 hours prior being polished to 6 mm long×4 mm in diameter using 600 grit sand paper. Compression test was conducted using an Instron Universal Tester Model 4400R with crosshead speed 5 mm/min. Six specimens were tested for each set of sample.

Diametral Tensile Strength: The specimens were prepared by filling the paste into a stainless-steel mold with a dimension of Ø6×3 mm, and then photo-curing the paste using Spectrum 800 lamp at intensity of 550 mW/cm$^2$ on both ends. The cured specimen was removed from the mold and stored in deionized water at 37° C. for 24 hours before subjecting to mechanical testing on an Instron Universal Tester Model 4400R in compression mode with a crosshead speed of 10 mm/min. The compressive load was applied in the diameter direction onto the specimen. The peak load at which the specimen broke was used to calculate the DTS expressed in MPa unit. Six specimens were tested for each set of sample.

EXAMPLES

The following components were used herein:
PENTA: Dipentaerythritol pentaacrylate phosphoric acid ester;

UDMA: 1,6-Bis [methacryloyloxyethoxycarbonylamino]-2,4,4-tromethylhexane;

OEMA: 4,4'-Oxydiphenylether 1,1',6,6'-tetracarboxylic acid-1,1'-(2-methacryloxy)dimethacrylate;

TMPTMA: Trimethylolpropane Trimethacrylate;

HEMA: 2-Hydroxyethyl methacrylate;

AHPMA: 3-(Acryloyloxy) 2-hydroxypropyl methacrylate;

CQ: Camphorquinone;

L-TPO: Diphenyl (2,4,6-trimethylbenzoyl)phosphine oxide;

DMABN: Dimethylaminobenzonitrile;

BHT: Butylated Hydroxytoluene;

Silanated BFBG-1: barium fluoroalumino borosilicate glass surface treated by γ-methacryloxypropyltrimethoxysilane;

Silanated BFBG-2: barium fluoroalumino borosilicate glass surface treated by γ-methacryloxypropyltrimethoxysilane; and Silanated SAFG: Silanated Strontium-AluminoSodium-Fluoro-Phosphorsilicate glass surface treated by γ-methacryloxypropyltrimethoxysilane.

A variety of different self-etching, self-adhesive restorative compositions were prepared.

Example 1

In Example 1, the self-etching, self-adhesive restorative composition was prepared by adding 35.42 parts silanated BFBG-1, 14.38 parts silanated BFBG-2, 1.48 parts of Aerosil R-972 and 0.72 parts of Cab-O-Sil TS-720 to resin blends consisting of 13.82 parts of PENTA, 12.96 parts of EBPADMA Urethane, 9.04 parts of UDMA, 4.80 parts of OEMA, 2.16 parts of TMPTMA, 2.16 parts of HEMA, 2.16 parts of AHPMA, 0.04 parts of Ca, 0.17 parts of L-TPO, 0.09 parts of DMABN, 0.03 parts of BHT, 0.35 parts of Univul M40, 0.13 parts of Irgacare MP, and 0.09 parts of flublau concentrate.

Example 2

As in Example 1, the self-etching, self-adhesive restorative composition for Example 2 was prepared by adding 34.32 parts silanated BFBG-2, 29.70 parts of silanated SAFG, 1.05 parts of Aerosil R-972 and 0.93 parts of Cab-O-Sil TS-720 to resin blends consisting of 6.19 parts of PENTA, 18.12 parts of UDMA, 2.82 parts of OEMA, 2.79 parts of TMPTMA, 3.55 parts of AHPMA, 0.03 parts of CQ, 0.12 parts of L-TPO, 0.06 parts of DMABN, 0.02 parts of BHT, 0.24 parts of Univul M40, and 0.06 parts of flublau concentrate.

Example 3

As in Example 2, the self-etching, self-adhesive restorative composition for Example 3 was prepared by adding 52.89 parts silanated BFBG-2, 1.62 parts of Aerosil R-972 and 0.48 parts of Cab-O-Sil TS-720 to resin blends consisting of 13.05 parts of PENTA, 10.35 parts of UDMA, 13.11 parts of OEMA, 2.70 parts of TMPTMA, 3.60 parts of HEMA, 1.35 parts of AHPMA, 0.05 parts of CQ, 0.16 parts of L-TPO, 0.08 parts of DMABN, 0.04 parts of BHT, 0.32 parts of Univul M40, 0.12 parts of Irgacare MP, and 0.08 parts of flublau concentrate.

Example 4

In Example 4, the self-etching, self-adhesive restorative composition was prepared by adding 31.80 parts of silanated BFBG-2, 18.82 parts of silanated SAFG, and 2.39 parts of Cab-O-Sil TS-720 to resin blends consisting of 13.63 parts of PENTA, 13.16 parts of EBPADMA Urethane, 5.64 parts of UDMA, 3.36 parts of OEMA, 3.76 parts of TMPTMA, 3.76 parts of HEMA, 2.82 parts of AHPMA, 0.04 parts of CQ, 0.17 parts of L-TPO, 0.08 parts of DMABN, 0.03 parts of BHT, 0.33 parts of Univul M40, 0.13 parts of Irgacare MP, and 0.08 parts of flublau concentrate.

Example 5

As in Example 4, the self-etching, self-adhesive restorative composition for Example 5 was prepared by adding 52.89 parts silanated BFBG-2, 1.62 parts of Aerosil R-972 and 0.48 parts of Cab-O-Sil TS-720 to resin blends consisting of 13.05 parts of PENTA, 12.44 parts of UDMA, 8.78 parts of OEMA, 3.60 parts of TMPTMA, 3.60 parts of HEMA, 2.70 parts of AHPMA, 0.04 parts of CQ, 0.16 parts of L-TPO, 0.08 parts of DMABN, 0.03 parts of BHT, 0.32 parts of Univul M40, 0.12 parts of Irgacare MP, and 0.08 parts of flublau concentrate.

Example 6

In Example 6, the self-etching, self-adhesive restorative composition was prepared by adding 52.92 parts of silanated BFBG-2, 1.56 parts of Aerosil R-972 and 0.52 parts of Cab-O-Sil TS-720 to resin blends consisting of 13.05 parts of PENTA, 12.60 parts of EBPADMA Urethane, 3.21 parts of UDMA, 5.40 parts of OEMA, 3.60 parts of TMPTMA, 3.60 parts of HEMA, 2.70 parts of AHPMA, 0.04 parts of CQ, 0.16 parts of L-TPO, 0.08 parts of DMABN, 0.03 parts of BHT, 0.32 parts of Univul M40, 0.12 parts of Irgacare MP, and 0.08 parts of flublau concentrate.

TABLE 1

Adhesive and Physical Properties of Self-Etching, Self-Adhesive Restorative Formulations

| Component | Comparative Example - TPH$^3$ FLOW | Example 1 | Example 2 | Example 3 | Example 4 | Example 5 | Example 6 |
|---|---|---|---|---|---|---|---|
| Shear Bond Strength to Dentin, MPa (s.d.) | — | 20.1 (5.3) | 13.4 (3.7) | 28.6 (5.7) | 20.0 (8.2) | 25.8 (4.6) | 25.3 (6.4) |
| Shear Bond Strength to Enamel, MPa (s.d.) | — | — | 14.5 (4.1) | 18.5 (4.1) | 16.6 (4.3) | 19.2 (6.3) | 17.1 (4.1) |
| Diametral Tensile Strength, MPa (s.d.) | 46.6 (2.2) | 52.8 (2.3) | 54.5 (4.3) | 57.5 (3.0) | 53.9 (4.2) | 57.8 (7.4) | 50.9 (0.8) |
| Compressive Strength, MPa (s.d.) | 330 (13) | 274 (6) | 315 (7) | 350 (17) | 316 (22) | 358 (34) | 378 (23) |
| Compressive Modulus, MPa (s.d.) | 2320 (132) | 3980 (647) | 4794 (193) | 4941 (265) | 4352 (224) | 4357 (468) | 4039 (728) |
| Transverse strength, MPa (s.d.) | 103 (11) | 113 (5) | 117 (12) | 95 (16) | 119 (17) | 125 (6) | 110 (17) |
| Flexural Modulus, MPa (s.d.) | 4490 (158) | 4801 (144) | 6302 (191) | 5619 (322) | 5816 (189) | 5843 (299) | 5134 (154) |
| Barcol Hardness (Hard) | 67 | 71 | 76 | 78 | 74 | 75 | 75 |

As shown in Table 1, the self-etching and self-adhesive composition described herein exhibited good bond strengths to tooth structures and improved mechanical properties. The self-etching and self-adhesive compositions are innovative flowable composites designed to eliminate the need for a separate adhesive placement/curing step. Therefore, no separate etchant, primer, or adhesive is needed for the composition to properly adhere to a tooth structure. The unique combination of a polymerization compound containing phosphoric acid functionality, such as PENTA, and another polymerization compound containing a carboxylic acid functionality, such as OEMA, as dual adhesion-promoting monomers in the resin blend greatly enhances its self-etching and self-adhesive capabilities due to the synergized adhesion properties generated from micro-mechanical bonding and chemical bonding. The initiator and resin system have also been optimized to achieve a fast polymerization rate, high crosslinking density, besides providing good overall adhesion property to the tooth substrate.

TABLE 2

Material Properties after Storage at 50° C.
Properties of Example 5 after 50° C. Storage

| Properties | RT Stored | 17 Days at 50° C. | 25 Days at 50° C. | 34 Days at 50° C. |
|---|---|---|---|---|
| Shear Bond Strength to Dentin, MPa (s.d.) | 25.8 (4.6) | 23.3 (4.1) | 22.2 (4.6) | 22.5 (5.6) |
| Shear Bond Strength to Enamel, MPa (s.d.) | 19.2 (6.3) | 17.0 (4.0) | 18.2 (3.7) | 15.5 (2.7) |
| Consistency (mm) | 27 | 27 | 27 | 27 |
| Extrusion Force (kgf) | 2.4 | 2.5 | 2.4 | 2.5 |
| Compressive Strength, MPa (s.d.) | 358 (34) | 361 (16) | 379 (13) | 387 (27) |
| Compressive Modulus, MPa (s.d.) | 4357 (468) | 4556 (379) | 4020 (604) | 4009 (466) |

The shelf-life stability of dental restorative composition is also greatly important to the product's performance and efficacy. Table 2 shows that the self-etching and self-adhesive composition paste of Example 5 stored at 50° C. for 17, 25, and 34 days, demonstrated no significant changes in appearance, compressive strength (around 370 MPa), extrusion force (maintains 2.4 to 2.5 kgf), and FTIR spectrum (not shown). The pastes' consistency remained at 27 mm, disregarding different storage periods at about 50° C. Furthermore, no statistically significant differences were found for shear bond strength to un-etched, un-primed dentin and enamel for Example 5 stored at about 50° C. for 17, 25, and 34 days, when compared with baseline.

Additionally, internal clinical evaluation of self-etching and self-adhesive composition that underwent shelf life stability was conducted by dispensing material onto a mix pad as well as into a class I molar cavity preparation in a Viade typodont tooth. In addition to visual observation, extrusion force, rheology and manipulation of the materials were compared. There was no distinguishable difference among samples during the visual observation of the material out of the syringe, during manipulation and after curing. All of the tested syringes of the self-etching and self-adhesive composition required similar extrusion force to dispense. The post extrusion force flow of the material was comparable between the samples as well. All of the aged materials exhibited similar rheology. There was no observable evidence of any material separation, clumping, or variation in shade.

The unique and innovative features of the self-etching and self-adhesive compositions described herein include 1) that it does not require a separate adhesive placement/curing steps before its placement (therefore no separate etchant, primer, or adhesive is needed); 2) one-part, shelf-stable, non-aqueous compositions can be developed. The self-etching and self-adhesive compositions also adapt to the cavity wall very well without the use of hand instruments and is very user friendly as it provides tremendous reduction in both placement time and technique-sensitivity, when compared with the use of a separate adhesive placement/curing steps that may involve etching, rinsing, drying, priming, before the final bonding agent can be applied and cured.

It will be appreciated that various of the above-disclosed compositions and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

I claim:
1. A dental composition consisting of:
a first polymerizable compound having at least one phosphorus acidic containing group,
a second polymerizable compound having at least one carboxylic acid group,
a copolymerizable (meth)acrylate monomer,
a filler system, and
a polymerization initiator system,
wherein first polymerizable compound with at least one phosphorus containing acidic group is present in the dental composition in an amount of from about 3 weight percent to about 50 weight percent based on a resin matrix, the second polymerizable compound with at least one carboxylic acid group is a free radically polymerizable compound and is present in the dental composition in an amount of from about 1 weight percent to about 50 weight percent based on the resin matrix, the copolymerizable (meth)acrylate monomer is present in the dental composition in an amount of from about 50 weight percent to about 95 weight percent based on the resin matrix, the filler system is present in the dental composition in an amount of from about 40 weight percent to about 85 weight percent based on the dental composition, the polymerization initiator system is present in the dental composition in an amount of from about 0.05 weight percent to about 1 weight percent based on the dental composition, and
wherein the second polymerizable compound having at least one carboxylic acid group is 4,4'-Oxydiphenylether 1,1',6,6'-tetracarboxylic acid-1,1'-(2-methacryloxy) dimethacrylate (OEMA),
wherein the polymerization initiator system is a dual-photoinitiator system having camphorquinone (CQ) and diphenyl (2,4,6-trimethylbenzoyl) phosphine oxide (L-TPO).
2. The dental composition according to claim 1, wherein the composition is capable of being applied directly to a tooth structure without any application of a separate adhesive or separate curing step prior to the direct application of the composition.

3. The dental composition of claim 1, wherein the first polymerizable compound having at least one phosphorus containing acidic group is 2-(methacryloyloxyehtyl)phenyl hydrogenphosphate (Phenyl-P), 2-hydroxyehtyl methacryl dihydrogenphosphate (HEMA Phosphate), glycerol phosphate dimethacrylate (GPDM), dipentaerythritiol pentacrylate phosphoric acid ester (PENTA), di-2-hydroxyethyl methacryl hydrogenphophate (di-HEMA Phosphate), or mixtures thereof.

4. The dental composition of claim 1, wherein the copolymerizable (meth)acrylate monomer is as methyl methacrylate, isopropyl methacrylate, ethyl acrylate, triethylenegylcol dimethacrylate, n-hexyl acrylate, stearyl acrylate, allyl acrylate, glycerol diacrylate, glycerol triacrylate, ethyleneglycol diacrylate, diethyleneglycol diacrylate, tetraethylene glycol di(meth)acrylate, 1,3-propanediol diacrylate, 3-(acryloyloxy)-2-hydroxypropyl methacrylate, 1,3-propanediol dimethacrylate, trimethylolpropanetri(meth)acrylate, 1,2,4-butanetriol trimethacrylate, 1,4-cyclohexanediol diacrylate, 1,6-hexanediol di(meth)acrylate, pentaerythritol triacrylate, pentaerythritol tetraacrylate, pentaerythritol tetramethacrylate, sorbitol hexacrylate, 2,2-bis [4-(2-hydroxy-3-acryloyloxypropoxy) phenyl]propane; 2,2-bis [4-(2-hydroxy-3-methacryloyloxypropoxy)phenyl]propane (Bis-GMA); 2,2-bis[4-(acryloyloxy-ethoxy)phenyl]propane; 2,2-bis[4-(methacryloyloxy-ethoxy)phendyl]propane (or ethoxylated bisphenol A-dimethacrylate) (EBPADMA), polycarbonate dimethacrylate (PCDMA), 2,7,7,9,15-pentamethy-4, 13 dioxo-3,14 dioxa-5,12-diaza hexadecane-1, diyldimethacrylate, urethane di(meth)acrylate (UDMA), bis-acrylates and bis-methacrylates of polymethylene glycols, or mixtures thereof.

5. The dental composition of claim 1, wherein the filler system is strontium silicate, strontium borosilicate, barium silicate, barium borosilicate, barium fluoroalumino borosilicate glass, barium alumino borosilicate, calcium silicate, calcium alumino sodium fluoro phosphor-silicate lanthanum silicate, alumino silicate, silicon nitrides, titanium dioxide, fumed silica, colloidal silica, quartz, kaolin ceramics, calcium hydroxy apatite, zirconia, barium alumino fluoro borosilicate glass, or mixtures thereof.

6. A method, comprising:
removing a carious portion of a tooth structure to create a cavity,
cleaning the created tooth cavity,
applying a dental composition directly into the cleaned tooth cavity, and
curing the dental composition,
wherein the dental composition consists of a first polymerizable compound having at least one phosphorus containing acidic group, a second polymerizable compound having at least one carboxylic acid group, a copolymerizable (meth)acrylate monomer, a filler system, and a polymerization initiator system,
wherein first polymerizable compound with at least one phosphorus containing acidic group is present in the dental composition in an amount of from about 3 weight percent to about 50 weight percent based on a resin matrix, the second polymerizable compound with at least one carboxylic acid group is a free radically polymerizable compound is present in the dental composition in an amount of from about 1 weight percent to about 50 weight percent based on the resin matrix, the copolymerizable (meth)acrylate monomer is present in the dental composition in an amount of from about 50 weight percent to about 95 weight percent based on the resin matrix, the filler system is present in the dental composition in an amount of from about 40 weight percent to about 85 weight percent based on the dental composition, the polymerization initiator system is present in the dental composition in an amount of from about 0.05 weight percent to about 1 weight percent based on the dental composition, and
wherein the second polymerizable compound having at least one carboxylic acid group is 4,4'-Oxydiphenylether 1,1',6,6'-tetracarboxylic acid-1,1'-(2-methacryloxy) dimethacrylate (OEMA),
wherein the polymerization initiator system is a dual-photoinitiator system having camphorquinone (CQ) and diphenyl (2,4,6-trimethylbenzoyl) phosphine oxide (L-TPO).

7. The method of claim 6, wherein the composition is capable of being applied directly to a tooth structure without any application of a separate adhesive or separate curing step prior to the direct application of the composition.

8. The method of claim 6, wherein the first polymerizable compound having at least one phosphorus containing acidic group is 2-(methacryloyloxyehtyl)phenyl hydrogenphosphate (Phenyl-P), 2-hydroxyehtyl methacryl dihydrogenphosphate (HEMA Phosphate), glycerol phosphate dimethacrylate (GPDM), dipentaerythritiol pentacrylate phosphoric acid ester (PENTA), di-2-hydroxyethyl methacryl hydrogenphophate (di-HEMA Phosphate), or mixtures thereof.

9. The method of claim 6, wherein the copolymerizable (meth)acrylate monomer is as methyl methacrylate, isopropyl methacrylate, ethyl acrylate, triethyleneglycol dimethacrylate, n-hexyl acrylate, stearyl acrylate, allyl acrylate, glycerol diacrylate, glycerol triacrylate, ethyleneglycol diacrylate, diethyleneglycol diacrylate, tetraethylene glycol di(meth)acrylate, 1,3-propanediol diacrylate, 3-(acryloyloxy)-2-hydroxypropyl methacrylate, 1,3-propanediol dimethacrylate, trimethylolpropanetri(meth)acrylate, 1,2,4-butanetriol trimethacrylate, 1,4-cyclohexanediol diacrylate, 1,6-hexanediol di(meth)acrylate, pentaerythritol triacrylate, pentaerythritol tetraacrylate, pentaerythritol tetramethacrylate, sorbitol hexacrylate, 2,2-bis [4-(2-hydroxy-3-acryloyloxypropoxy) phenyl]propane; 2,2-bis [4-(2-hydroxy-3-methacryloyloxypropoxy)phenyl]propane (Bis-GMA); 2,2-bis[4-(acryloyloxy-ethoxy)phenyl]propane; 2,2-bis[4-(methacryloyloxy-ethoxy)phendyl]propane (or ethoxylated bisphenol A-dimethacrylate) (EBPADMA), polycarbonate dimethacrylate (PCDMA), 2,7,7,9,15-pentamethy-4, 13 dioxo-3,14 dioxa-5,12-diaza hexadecane-1, diyldimethacrylate, urethane di(meth)acrylate (UDMA), bis-acrylates and bis-methacrylates of polymethylene glycols, or mixtures thereof.

10. The method of claim 6, wherein the filler system is strontium silicate, strontium borosilicate, barium silicate, barium borosilicate, barium fluoroalumino borosilicate glass, barium alumino borosilicate, calcium silicate, calcium alumino sodium fluoro phosphor-silicate lanthanum silicate, alumino silicate, silicon nitrides, titanium dioxide, fumed silica, colloidal silica, quartz, kaolin ceramics, calcium hydroxy apatite, zirconia, barium alumino fluoro borosilicate glass, or mixtures thereof.

11. A dental composition consisting of:
a first polymerizable compound having at least one phosphorus acidic containing group,
a second polymerizable compound having at least one carboxylic acid group, a copolymerizable (meth)acrylate monomer,
a filler system,
a polymerization initiator system, and
at least one of a polymerization accelerator, ultra-violet stabilizers, fluorescent agents, opalescent agents, pigments viscosity modifiers, fluoride-releasing agents, antimicrobial agents, or polymerization inhibitors,
wherein first polymerizable compound with at least one phosphorus containing acidic group is present in the dental composition in an amount of from about 3 weight percent to about 50 weight percent based on a resin matrix, the second polymerizable compound with at least one carboxylic acid group is a free radically polymerizable compound and is present in the dental composition in an amount of from about 1 weight percent to about 50 weight percent based on the resin matrix, the copolymerizable (meth)acrylate monomer is present in the dental composition in an amount of from about 50 weight percent to about 95 weight percent based on the resin matrix, the filler system is present in the dental composition in an amount of from about 40 weight percent to about 85 weight percent based on the dental composition, the polymerization initiator system is present in the dental composition in an amount of from about 0.05 weight percent to about 1 weight percent based on the dental composition, and
wherein the second polymerizable compound having at least one carboxylic acid group is 4,4'-Oxydiphenylether 1,1',6,6'-tetracarboxylic acid-1,1'-(2-methacryloxy) dimethacrylate (OEMA),
wherein the polymerization initiator system is a dual-photoinitiator system having camphorquinone (CQ) and diphenyl (2,4,6-trimethylbenzoyl) phosphine oxide (L-TPO).

* * * * *